(12) United States Patent
Varadhachary et al.

(10) Patent No.: US 7,026,295 B2
(45) Date of Patent: Apr. 11, 2006

(54) LACTOFERRIN IN THE REDUCTION OF CIRCULATING CHOLESTEROL, VASCULAR INFLAMMATION, ATHEROSCLEROSIS AND CARDIOVASCULAR DISEASE

(75) Inventors: Atul Varadhachary, Houston, TX (US); Peter Glynn, Houston, TX (US); Yenyun Wang, Houston, TX (US); Jose Engelmayer, Houston, TX (US)

(73) Assignee: Agennix Incorporated, Houston, TX (US)

( * ) Notice: Subject to any disclaimer, the term of this patent is extended or adjusted under 35 U.S.C. 154(b) by 0 days.

(21) Appl. No.: 10/728,275

(22) Filed: Dec. 4, 2003

(65) Prior Publication Data
US 2004/0152623 A1  Aug. 5, 2004

Related U.S. Application Data

(60) Provisional application No. 60/498,337, filed on Aug. 27, 2003, provisional application No. 60/430,867, filed on Dec. 4, 2002.

(51) Int. Cl.
*A61K 38/00* (2006.01)

(52) U.S. Cl. .............................. 514/12; 514/2; 514/21; 530/350; 530/300; 435/7.1

(58) Field of Classification Search .................... 514/2, 514/12, 21; 530/350, 300; 435/7.1
See application file for complete search history.

(56) References Cited

U.S. PATENT DOCUMENTS

| | | | |
|---|---|---|---|
| 6,333,311 B1 * | 12/2001 | Nuijens et al. | ................ 514/12 |
| 2002/0119928 A1 | 8/2002 | McAnalley | |
| 2003/0060425 A1 | 3/2003 | Ahlem et al. | |

FOREIGN PATENT DOCUMENTS

WO   WO-0241912   5/2002

OTHER PUBLICATIONS

Cianflone et al., Atherosclerosis, vol. 120, 1996, pp. 101-114.*
Kajikawa et al, "Lactoferrin inhibits Cholestrol Accumulation in Macrophages Mediated by Acetylated or Oxidized Low-Density Lipoproteins," Biochim Biophys Acta. Jun. 23, 1994; 1213(1): 82-90.
Croy et al, "All three LDL Receptor Homology Regions of the LDL Receptor-related Protein Binf Multiple Ligands," Biochemistry Nov. 11, 2003; 42(44): 13049-13057.
Huettinger, M. et al, "The LDL-receptor Family: Lactoferrin and Lipid Metabolism," Adv Exp. Med Biol. 1998; 443: 107-11.
Huettinger, m. et al, "Characteristics of Chylomicron Remnant Uptake into Rat Liver," Clin Biochem. Apr. 1988; 21(2): 87-92.
van Dijk MC et al, "Recognition of Chylomicron Remnants and Beta-Migrating very-low Density Lipoproteins by the Remnant Receptor of Parenchymal Liver Cells is Distinct from the Liver Alpha 2-Macroglobulin Recognition Site," Biochem J. 1991 No. 1; 279(Pt. 3): 863-70.
Benezra, M. et al, "A Synthetic Heparin-Mimicking Polyanionic Compound Binds to the LDL Receptor-related Protein and inhibits Vascular Smooth Muscle Cell Proliferation," J. Cell Biochem 2001; 81(1): 114-27.
Hayashida et al, "Bovine Lactoferrin has a Nitric Oxide-dependent Hypotensive Effect in Rats," Am J Physiol Regul Integr Comp Physiol. Feb. 2004; 286(2): R359-65.
Llirbat et al, "Normal and Inhibited Cholesterol Synthesis in the Cultured Rat Embryo," Journal of Lipid Research vol. 38, pp. 22-34 (1997).

* cited by examiner

*Primary Examiner*—Kathleen M. Kerr
*Assistant Examiner*—Hope Robinson
(74) *Attorney, Agent, or Firm*—Fulbright & Jaworski L.L.P.

(57) ABSTRACT

The present invention relates to methods of using lactoferrin (LF) to reduce circulating levels of cholesterol and vascular inflammation, in order to treat, prevent or reduce the incidence of atherosclerosis and cardiovascular disease.

23 Claims, 5 Drawing Sheets

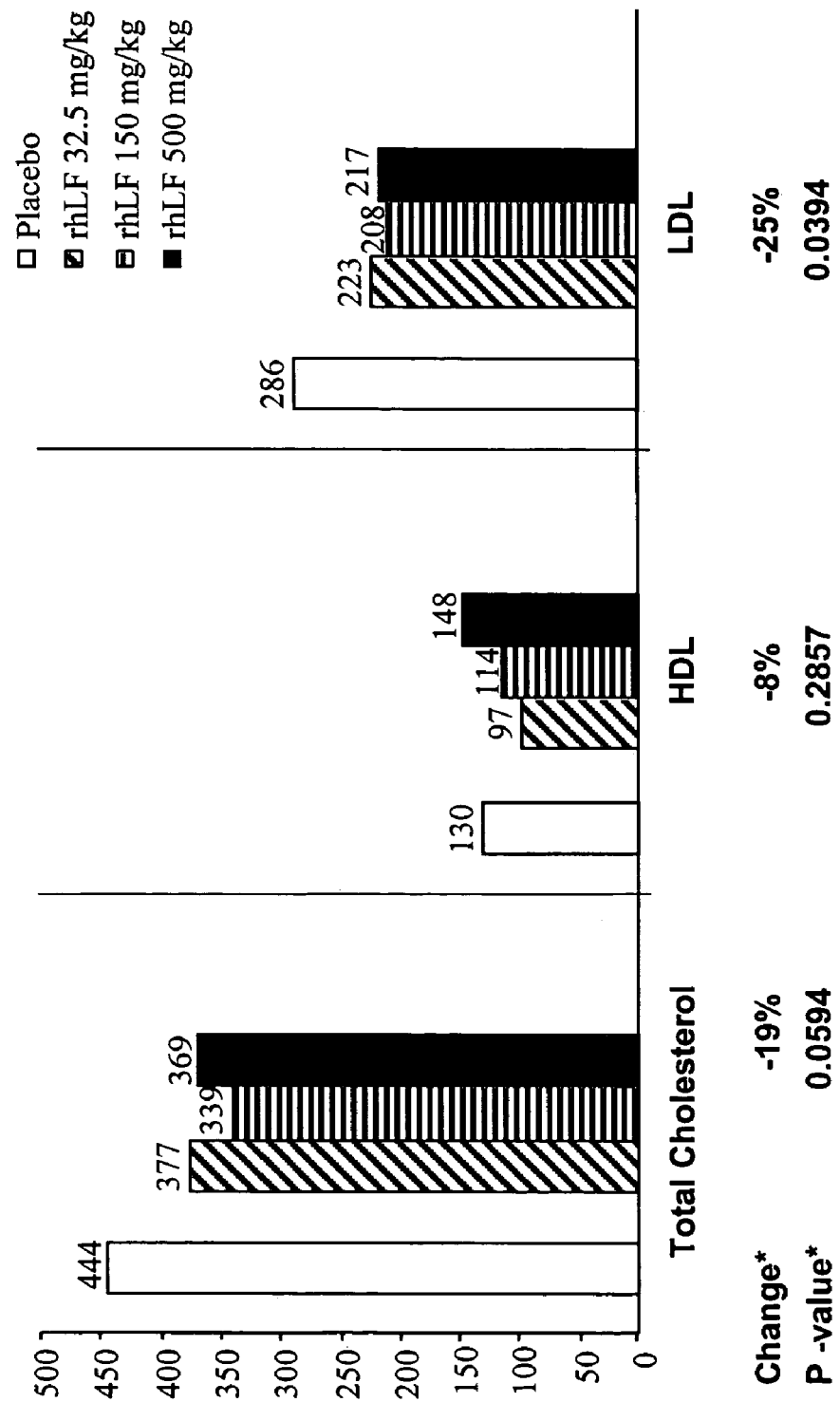

LACTOFERRIN IN THE REDUCTION OF CIRCULATING CHOLESTEROL, VASCULAR INFLAMMATION, ATHEROSCLEROSIS AND CARDIOVASCULAR DISEASE

CROSS-REFERENCE TO RELATED APPLICATIONS

This application claims priority to U.S. Provisional Application Nos. 60/498,337 filed Aug. 27, 2003 and 60/430,867 filed Dec. 4, 2002 which are incorporated herein by reference.

TECHNICAL FIELD

The present invention relates to methods of using lactoferrin (LF) to reduce circulating levels of cholesterol and vascular inflammation, in order to treat, prevent or reduce the incidence of atherosclerosis and cardiovascular disease. More particularly, the present invention relates to methods of reducing circulating levels of cholesterol and vascular inflammation by administering a composition of lactoferrin.

BACKGROUND OF THE INVENTION

According to current estimates, 61,800,000 people in America have one or more forms of cardiovascular disease. These diseases claimed 958,775 lives in 1999 (40.1 percent of all deaths). Atherosclerosis is a leading form of cardiovascular disease, which involves the slow build-up of fatty plaques on the arterial wall. This build-up can damage the vascular endothelium causing inflammation, a narrowing of the arteries and potential arterial blockages that can result in heart attacks. Atherosclerosis is a complex disease that starts in childhood and often progresses when people grow older. In some people it progresses rapidly, even in their third decade. Elevated levels of cholesterol, in particular LDL (low-density lipoprotein), and triglycerides in the blood have been associated with the development of fatty plaques, which can lead to generalized vascular damage, atherosclerosis and eventually heart attack. Atherosclerosis and cardiac disease is also associated with increased cardiovascular inflammation, specifically as measured by levels of circulating C-reactive protein (CRP).

One key strategy for reducing the risk of atherosclerosis has been to lower the levels of cholesterol in the blood. Cholesterol levels in many people can be controlled by diet, but for many patients diet changes alone are insufficient to reduce high cholesterol. In recent years, cholesterol lowering drugs such as Zocor® (simvastatin) and Lipitor® (atorvastatin) have been increasingly prescribed to help patients lower their cholesterol levels. These drugs however, are not equally effective in all patients and frequently are associated with significant adverse side effects. A second key emerging strategy is the reduction of CRP, an important indicator of vascular inflammation and independently associated with increased risk of cardiovascular disease. Thus, safer and more effective treatments for lowering cholesterol and for reducing the vascular inflammation associated with atherosclerosis are of great potential value.

Lactoferrin is a single chain metal binding glycoprotein. Many cell types, such as monocytes, macrophages, lymphocytes, and brush-border cells in the intestine, are known to have lactoferrin receptors. Lactoferrin is found mainly in external secretions of mucosal epithelia such as breast milk, saliva, tears, bile, and pancreatic fluid and has a wide array of functions related to host primary defense mechanisms. For example, lactoferrin has been reported to activate natural killer (NK) cells, induce colony stimulating activity, activate polymorphonuclear neutrophils (PMN), regulate granulopoeisis, enhance antibody-dependent cell cytotoxicity, stimulate lymphokine-activated killer (LAK) cell activity, and potentiate macrophage toxicity.

Recombinant human lactoferrin has previously been described as being purified after expression in a variety of prokaryotic and eukaryotic organisms including aspergillus (U.S. Pat. No. 6,080,559), cattle (U.S. Pat. No. 5,919,913), rice, corn, Sacharomcyes (U.S. Pat. No. 6,228,614) and Pichia pastoris (U.S. Pat. Nos. 6,455,687, 6,277,817, 6,066, 469). Also described are expression systems for the expression of full-length human lactoferrins (e.g., U.S. Pat. No. 6,100,054). In all cases, part of the teaching is expression of the full length cDNA and purification of the intact protein whose N-terminal, after processing of the leader peptide, is the amino acid glycine. Nuijens et al. (U.S. Pat. No. 6,333, 311) separately describe variants of human lactoferrin but their focus is limited to deletion or substitution of arginine residues found in the N-terminal domain of lactoferrin.

The present invention is the first to use a lactoferrin composition as a means of reducing cholesterol and cardiovascular inflammation and for treating or reducing atherosclerosis and cardiovascular disease.

BRIEF SUMMARY OF THE INVENTION

The present invention is directed to a method for modulating circulating levels of cholesterol and reducing the vascular inflammation associated with atherosclerosis and cardiovascular disease. The method of treatment involves administration of a lactoferrin composition.

The lactoferrin composition, which is dispersed in a pharmaceutically acceptable carrier, comprises lactoferrin or an N-terminal lactoferrin variant in which at least the N-terminal glycine residue is truncated or substituted. The lactoferrin is mammalian lactoferrin, more particularly, the lactoferrin is human or bovine. Yet further, the lactoferrin is recombinant lactoferrin. N-terminal lactoferrin variants include variants that at least lack the N-terminal glycine residue or contain a substitution at the N-terminal glycine residue. The substitution can comprise substituting a natural or artificial amino acid residue for the N-terminal glycine residue. For example, the substitution can comprise substituting a positive amino acid residue or a negative amino acid residue for the N-terminal glycine residue or substituting a neutral amino acid residue other than glycine for the N-terminal glycine residue. Other N-terminal lactoferrin variants include lactoferrin lacking one or more N-terminal residues or having one or more substitutions in the N-terminal. In specific embodiments, the N-terminal lactoferrin variant comprises at least 1% of the lactoferrin composition, at least 5% of the lactoferrin composition, at least 10% of the lactoferrin composition, at least 25% of the lactoferrin composition, at least 50% of the lactoferrin composition or any range in between.

The amount of the lactoferrin that is administered is about 1 ng to about 20 g per day, more preferably, the amount is about 0.1 g to about 5 g per day. More particularly, the composition is a solution, capsule or a tablet having a lactoferrin concentration of about 0.1% to about 100%.

In further embodiments, a metal chelator dispersed in a pharmaceutically acceptable carrier can also be administered with the lactoferrin composition. Preferred metal chelator include, but are not limited to ethylenediaminetetraacetic acid (EDTA) or [ethylenebis(oxyethylenenitrilo)]

tetraacetic acid (EGTA). More preferably, the metal chelator is EDTA. The amount of EDTA that is administered is about 1 ng to about 1 g per day.

An embodiment of the present invention is a method of treating a cardiovascular disease comprising the step of administering to a subject a lactoferrin composition in an effective amount to provide an improvement in the cardiovascular disease, for example, atherosclerosis. The lactoferrin composition reduces the levels of circulating total cholesterol, low density lipoproteins (LDL), or very low density lipoproteins (VLDL). Still further, the lactoferrin composition increases the levels of circulating high density lipoproteins (HDL). In addition to modulating levels of cholesterol, the lactoferrin composition reduces the levels of vascular inflammation, circulating C-reactive protein (CRP), triglycerides, or proliferation of vascular smooth muscle cells. The lactoferrin composition may also reduce vascular spasms or vascular hyper-reactivity or promote endothelial integrity or healing. In further embodiments, the lactoferrin composition reduces the production or activity of pro-inflammatory cytokines.

The lactoferrin composition of the present invention can be administered parenterally, for example, subcutaneously, intramuscularly, intraperitoneally, intravenously, intraarterially, intramyocardially, transendocardially, transepicardially, or intrathecally.

In a further embodiment, the lactoferrin composition is administered orally. For oral administration, an antacid in combination with the lactoferrin composition can be administered. The lactoferrin can be formulated in a delayed release formulation. Still further, the lactoferrin composition can be formulated wherein release occurs in the small intestine or in the large intestine.

Another embodiment of the present invention is a method of modulating atherosclerosis in a subject comprising the step of administering to the subject a lactoferrin composition in an effective amount to modulate atherosclerosis in the subject. Modulating is reducing the incidence of atherosclerosis or reducing the severity of atherosclerosis. In further embodiments, the lactoferrin composition can be administered in combination with an anti-cholesterol agent or an anti-inflammatory agent. The anti-cholesterol agent is selected from the group consisting of cholesterol absorption inhibitors, bile acid sequestrants (cholestyramine, cholestipol and colesevalam), nicotinic acid, fibric acids (gemfibrozil, fenofibrate and clofibrate) and HMG-coA reductase inhibitors (lovastatin, pravastatin, simvastatin, fluvastatin, atorvastatin and cerivastatin).

Another embodiment is a method of preventing a cardiovascular disease in a subject at risk for developing a cardiovascular disease comprising the step of administering to the subject a lactoferrin composition in an amount sufficient to result in prophylaxis of the cardiovascular disease in the subject. The cardiovascular disease is atherosclerosis.

Still further, another embodiment is a method of reducing the risk of cardiovascular disease in a subject at risk for developing a cardiovascular disease comprising the step of administering to the subject a lactoferrin composition in an effective amount to result in a reduction of risk of the cardiovascular disease in the subject. The cardiovascular disease is atherosclerosis.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated that the conception and specific embodiment disclosed may be readily utilized as a basis for modifying or designing other structures for carrying out the same purposes of the present invention. It should also be realized that such equivalent constructions do not depart from the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawings.

FIG. 3A shows the effect of rhLF on HDL, LDL and total cholesterol levels. FIG. 3B shows the effect on HDL/LDL ratio.

FIG. 4 shows a dose effect of rhLF on hyperlipidemia in mice.

DETAILED DESCRIPTION OF THE INVENTION

Figure 1:
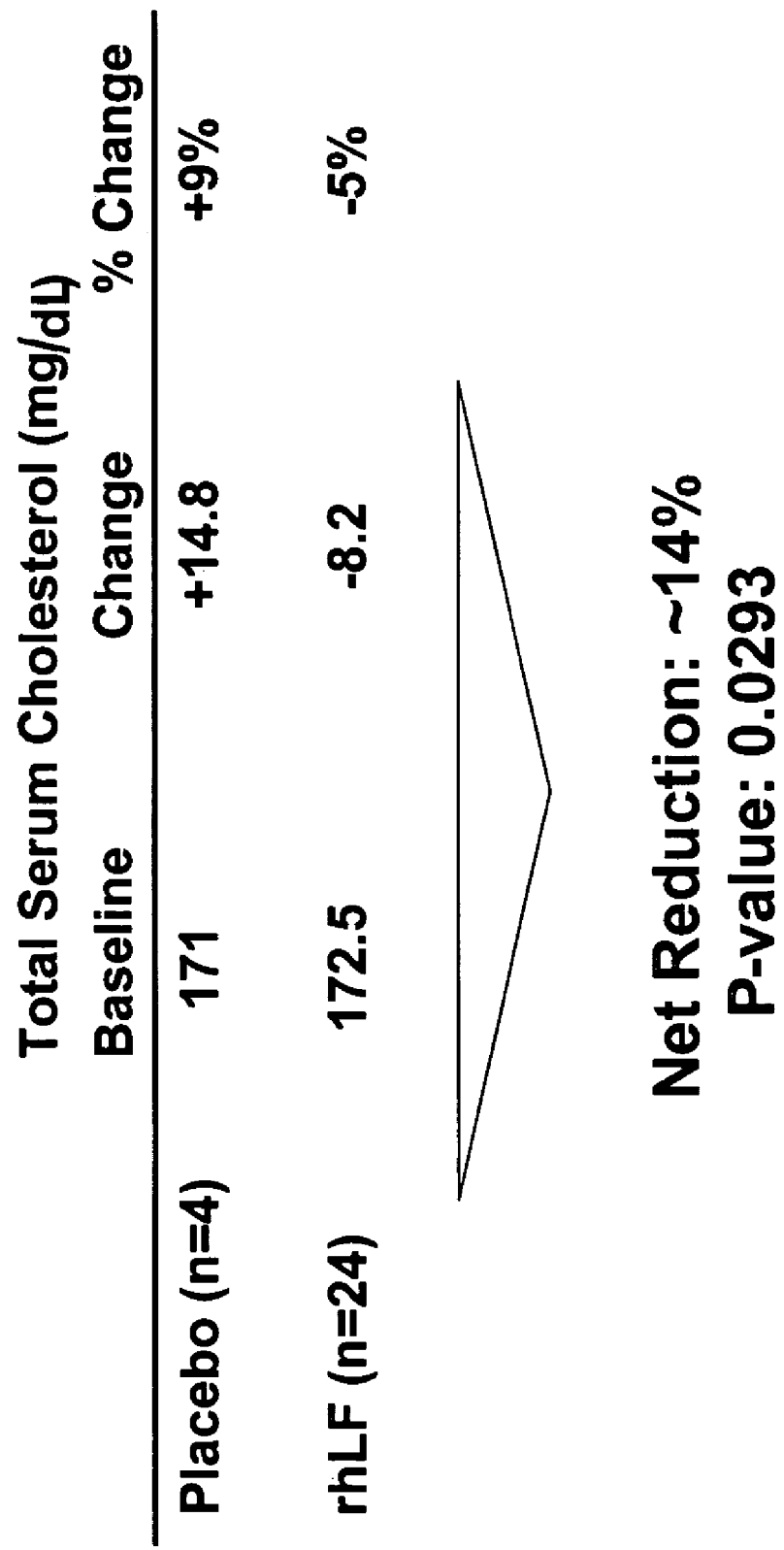
FIG. 1 shows the net reduction of total serum cholesterol in subjects receiving oral rhLF for seven days with respect to patients receiving placebo for seven days.

It is readily apparent to one skilled in the art that various embodiments and modifications can be made to the invention disclosed in this Application without departing from the scope and spirit of the invention.

As used herein, the use of the word "a" or "an" when used in conjunction with the term "comprising" in the claims and/or the specification may mean "one," but it is also consistent with the meaning of "one or more," "at least one," and "one or more than one." Still further, the terms "having", "including", "containing" and "comprising" are interchangeable and one of skill in the art is cognizant that these terms are open ended terms.

The term "atherosclerosis" as used herein includes a form of arteriosclerosis characterized by a combination of changes in the intima of arteries, such changes include, but are not limited to accumulation of lipids, complex carbohydrates, blood and blood products, fibrous tissue and calcium deposits. Yet further, atherosclerotic plaques can be characterized into at least two areas. One type is characterized by prominent proliferation of cells with small accumulations of lipids. The second type consists mostly of intracellular and extracellular lipid accumulation and a small amount of cellular proliferation.

The term "cardiovascular disease or disorder" as used herein refers to disease and disorders related to the cardiovascular or circulatory system. Cardiovascular disease and/or disorders include, but are not limited to, diseases and/or disorders of the pericardium, heart valves (e.g., incompetent valves, stenosed valves, rheumatic heart disease, mitral valve prolapse, aortic regurgitation), myocardium (e.g., coronary artery disease, myocardial infarction, heart failure, ischemic heart disease, angina) blood vessels (e.g., hypertension, arteriosclerosis, aneurysm) or veins (e.g., varicose veins, hemorrhoids). Yet further, one skill in the art recognizes that cardiovascular diseases and/or disorders can result from congenital defects, genetic defects, environmental influences (e.g., dietary influences, lifestyle, stress, etc.), and other defects or influences.

The term "chemokine" as used herein refers to small cytokines that are involved in the migration and activation of cells, for example phagocytic cells and lymphocytes. One of skill in the art realizes that chemokines play a central role in inflammatory and immune response processes.

The term "cholesterol" as used herein refers to the monohydric alcohol form, which is a white, powdery substance that is found in all animal cells and in animal-based foods (not in plants). Cholesterol is an essential nutrient necessary for many functions, including the following: repairing cell membranes, manufacturing vitamin D on the skin's surface, production of hormones, such as estrogen and testosterone, and possibly helping cell connections in the brain that are important for learning and memory.

The term "chylomicron" as used herein refers to the largest in size and lowest in density of the triglyceride carrying lipoproteins.

The term "cytokine" as used herein refers to proteins that are made by cells that affect the behavior of other cells, for example stimulate or inhibit cell proliferation. For example, cytokines that are made by lymphocytes are often called lymphokines or interleukins. One of skill in the art realizes that the term cytokine is a generic term used in the literature to refer to proteins that are made by cells that can effect the behavior of other cells.

The term "effective amount" or "therapeutically effective amount" are interchangeable as used herein and refer to an amount that results in an improvement or remediation of the symptoms of the disease or condition.

The term "high-density lipoprotein" or "HDL" as used herein is the smallest and most dense type of cholesterol-carrying lipoprotein and is often referred to as the "good" cholesterol.

The term "intermediate density lipoprotein" or "IDL" as used herein refers to a triglyceride-carrying lipoprotein.

The term "lactoferrin" or "LF" as used herein refers to native or recombinant lactoferrin. Native lactoferrin can be obtained by purification from mammalian milk or colostrum or from other natural sources. Recombinant lactoferrin (rLF) can be made by recombinant expression or direct production in genetically altered animals, plants, fungi, bacteria, or other prokaryotic or eukaryotic species, or through chemical synthesis.

The term "lactoferrin composition" as used herein refers to a composition having lactoferrin, a portion or part of lactoferrin, an N-terminal lactoferrin variant, or a combination thereof.

The term "lipid" as used herein refers to the building blocks of any of the fats or fatty substances found in animals and plants, which are characterized by their insolubility in water and solubility in fat solvents such as alcohol, ether and chloroform. Lipids include fats (e.g., esters of fatty acids and glycerol); lipoids (e.g., phospholipids, cerebrosides, waxes) and sterols (e.g., cholesterol).

The term "lipoproteins" as used herein are protein spheres that transport cholesterol, triglyceride, or other lipid molecules through the bloodstream. Lipoproteins are categorized into five types according to size and density. They can be further defined by whether they carry cholesterol [the two smaller lipoproteins (HDL and LDL)] or triglycerides [the three largest lipoproteins (IDL, VLDL, and chylomicrons)].

The term "low density lipoprotein" or "LDL" as used herein is a type of cholesterol-carrying lipoprotein which is often called the "bad" cholesterol.

The term "N-terminal lactoferrin variant" as used herein refers to lactoferrin wherein at least the N-terminal glycine has been truncated and/or substituted. N-terminal lactoferrin variants also include, but are not limited to deletion and/or substitution of one or more N-terminal amino acid residues, for example 1, 2, 3, 4, 5, 6, 7, 8, 9, 10, 11, 12, 13, 14, 15, or 16 N-terminal amino acid residues, etc. Thus, N-terminal lactoferrin variants comprise at least deletions or truncations and/or substitutions of 1 to 16 N-terminal amino acid residues. The deletion and/or substitution of at least the N-terminal glycine of lactoferrin mediates the same biological effects as full-length lactoferrin and/or may enhance lactoferrin's biological activity, for example by stimulating the production of various cytokines (e.g., IL-18, MIP-3α, GM-CSF or IFN-γ) by inhibiting various cytokines, (e.g., IL-2, IL-4, IL-5, IL-10, or TNF-α) by improving a cardiovascular disease, e.g., atherosclerosis, or the parameters relating to cardiovascular disease including circulating levels of total cholesterol, HDL, LDL, VLDL, trigylcerides and C-reactive protein (CRP).

The term "metal chelator" as used herein refers to a compound which binds metal. Metal chelators that can be used in the present invention include the divalent metal chelators, for example, ethylenediaminetetraacetic acid (EDTA), [ethylenebis (oxyethylenenitrilo)]tetraacetic acid (EGTA), 1,2-bis(2-aminophenoxy)ethane-N,N,N',N'-tetraacetic acid (BAPTA), hydroxyethlene triamine diacetic acid, (HEDTA) or salts thereof.

The term "oral administration" as used herein includes oral, buccal, enteral or intragastic administration.

The term "parenteral administration" as used herein includes any form of administration in which the compound is absorbed into the subject without involving absorption via the intestines. Exemplary parenteral administrations that are used in the present invention include, but are not limited to intramuscular, intravenous, intraperitoneal, intraocular, subcutaneous or intraarticular administration. Yet further, parenteral administration also includes administration into a surgical field.

The term "pharmaceutically acceptable carrier" as used herein includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the vectors or cells of the present invention, its use in therapeutic compositions is contemplated. Supplementary active ingredients also can be incorporated into the compositions.

The term "preventing" as used herein refers to minimizing, reducing or suppressing the risk of developing a disease state or parameters relating to the disease state or progression or other abnormal or deleterious conditions.

The term "statin" as used herein includes compounds that are HMG-CoA reductase inhibitors, for example, but not limited to simvastatin (Zocor®) and atorvastatin (Lipitor®). Thus, as used herein the terms "statin" and "HMG-CoA reductase inhibitor" are interchangeable.

The term "subject" as used herein, is taken to mean any mammalian subject to which a lactoferrin composition is administered according to the methods described herein. Thus, a skilled artisan realizes that a mammalian subject, includes, but is not limited to humans, monkeys, horses, pigs, cows, dogs, cats, rats and mice. In a specific preferred embodiment, the methods of the present invention are employed to treat a human subject. In more preferred embodiments, the subject has signs or indicators of atherosclerosis. These signs or indicators include, for example, the development of cholesterol plaques in the arteries and calcification, the extent of which can be determined by Sudan IV staining, or the development of foam cells in an artery or arterial spasm. Atherosclerosis also is characterized by a narrowing of the arteries detected by, for example, coronary angioplasty, ultrasound and ultrafast CT. In further embodiments, the subject is at risk of developing a cardiovascular disease. Thus, the subject may or may not be cognizant of their disease state or potential disease state and may or may not be aware that they are need of treatment (therapeutic treatment or prophylactic treatment).

The term "topical administration" as used herein includes, but is not limited to topical, dermal, or epidermal.

The term "total cholesterol" as used herein refers to the sum of three kinds of lipids: high-density lipoprotein (HDL), low-density lipoprotein (LDL), and triglycerides. Levels of serum total cholesterol of >200 mg/dl are levels that are an indicating risk factor for atherosclerosis and cardiovascular disease.

The term "triglycerides" as used herein are composed of fatty acid molecules and are the basic chemicals contained in fats in both animals and plants.

The term "treating" and "treatment" as used herein refers to administering to a subject a therapeutically effective amount of a recombinant human lactoferrin composition so that the subject has an improvement in a cardiovascular disease or the parameters relating to cardiovascular disease including circulating levels of total cholesterol, HDL, LDL, VLDL, trigylcerides and C-reactive protein (CRP). The improvement is any observable or measurable improvement. Thus, one of skill in the art realizes that a treatment may improve the patient condition, but may not be a complete cure of the disease.

The term "very low density lipoprotein" or "VLDL" as used herein refers to a triglyceride carrying lipoprotein.

A. Lactoferrin

The lactoferrin used according to the present invention can be obtained through isolation and purification from natural sources, for example, but not limited to mammalian milk. The lactoferrin is preferably mammalian lactoferrin, such as bovine or human lactoferrin. In preferred embodiments, the lactoferrin is produced recombinantly using genetic engineering techniques well known and used in the art, such as recombinant expression or direct production in genetically altered animals, plants or eukaryotes, or chemical synthesis. See, for example, U.S. Pat. Nos. 5,571,896; 5,571,697 and 5,571,691, which are herein incorporated by reference.

In certain aspects, the present invention provides lactoferrin variants having enhanced biological activities over natural LF and or rLF, e.g., the ability to stimulate and/or inhibit cytokines or chemokines. In particular, the invention provides variants of lactoferrin from which at least the N-terminal glycine residue has been substituted and/or truncated. The N-terminal lactoferrin variants may occur naturally or may be modified by the substitution or deletion of one or more amino acids.

The deletional variants can be produced by proteolysis of lactoferrin and/or expression of a polynucleotide encoding a truncated lactoferrin as described in U.S. Pat. No. 6,333,311, which is incorporated herein by reference.

Substitutional variants or replacement variants typically contain the exchange of one amino acid for another at one or more sites within the protein. Substitutions can be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); asparate (−3.5); asparagine (−3.5); lysine (−3.9); and arginine (−4.5).

It is known in the art that certain amino acids may be substituted by other amino acids having a similar hydropathic index or score and still result in a protein with similar biological activity, e.g., still obtain a biological functionally equivalent protein. In making such changes, the substitution of amino acids whose hydropathic indices are within ±2 is preferred, those that are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine −0.5); cysteine (−1.0); methionine (−1.3); valine (−1.5); leucine (−1.8); isoleucine (−1.8); tyrosine (−2.3); phenylalanine (−2.5); tryptophan (−3.4).

Still further, it is understood that an amino acid can be substituted for another having a similar hydrophilicity value and still obtains a biologically equivalent and immunologically equivalent protein. In such changes, the substitution of amino acids whose hydrophilicity values are within ±2 is preferred, those that are within ±1 are particularly preferred, and those within ±0.5 are even more particularly preferred.

Thus, in the present invention, substitutional variants or replacement can be produced using standard mutagenesis techniques, for example, site-directed mutagenesis as disclosed in U.S. Pat. Nos. 5,220,007; 5,284,760; 5,354,670; 5,366,878; 5,389,514; 5,635,377; 5,789,166, and 6,333,311, which are incorporated herein by reference. It is envisioned that at least the N-terminal glycine amino acid residue can be replaced or substituted with any of the twenty natural occurring amino acids, for example a positively charged amino acid (arginine, lysine, or histidine), a neutral amino acid (alanine, asparagine, cysteine, glutamine, glycine, isoleucine, leucine, methionine, phenylaline, proline, serine, threonine, tryptophan, tyrosine, valine) and/or a negatively charged amino acid (aspartic acid or glutamic acid). Still further, it is contemplated that any amino acid residue within the range of N1 to N16 can be replaced or substituted. It is envisioned that at least up to 16 of the N-terminal amino acids residues can be replaced or substituted as long as the protein retains it biological and/or functional activity, which is stimulating the production of various cytokines, (e.g., IL-18, MIP-3α, GM-CSF or IFN-γ) by inhibiting various cytokines, (e.g., IL-2, IL-4, IL-5, IL-10, and TNF-α) by improving a cardiovascular disease, e.g., atherosclerosis, or the parameters relating to cardiovascular disease including circulating levels of total cholesterol, HDL, LDL, VLDL, triglycerides and C-reactive protein (CRP). Thus, the N-terminal lactoferrin variants of the present invention are considered functional equivalents of lactoferrin.

In terms of functional equivalents, it is well understood by the skilled artisan that, inherent in the definition of a "biologically functional equivalent" protein is the concept that there is a limit to the number of changes that may be made within a defined portion of the molecule while retaining a molecule with an acceptable level of equivalent biological activity and/or enhancing the biological activity of the lactoferrin molecule. Biologically functional equivalents are thus defined herein as those proteins in which selected amino acids (or codons) may be substituted. Functional activity is defined as the ability of lactoferrin to stimulate or inhibit various cytokines or chemokines and/or by improving a cardiovascular disease, e.g., atherosclerosis, or the parameters relating to cardiovascular disease including circulating levels of total cholesterol, HDL, LDL, VLDL, triglycerides and C-reactive protein (CRP).

Still further, the N-terminal amino acid residues can be substituted with a modified and/or unusual amino acids. A table of exemplary, but not limiting, modified and/or unusual amino acids is provided herein below.

TABLE 1

Modified and/or Unusual Amino Acids

| Abbr. | Amino Acid | Abbr. | Amino Acid |
|---|---|---|---|
| Aad | 2-Aminoadipic acid | EtAsn | N-Ethylasparagine |
| BAad | 3-Aminoadipic acid | Hyl | Hydroxylysine |
| BAla | beta-alanine, beta-Amino-propionic acid | AHyl | allo-Hydroxylysine |
| Abu | 2-Aminobutyric acid | 3Hyp | 3-Hydroxyproline |
| 4Abu | 4-Aminobutyric acid, piperidinic acid | 4Hyp | 4-Hydroxyproline |
| Acp | 6-Aminocaproic acid | Ide | Isodesmosine |
| Ahe | 2-Aminoheptanoic acid | Aile | allo-Isoleucine |
| Aib | 2-Aminoisobutyric acid | MeGly | N-Methylglycine, sarcosine |
| BAib | 3-Aminoisobutyric acid | MeIle | N-Methylisoleucine |
| Apm | 2-Aminopimelic acid | MeLys | 6-N-Methyllysine |
| Dbu | 2,4-Diaminobutyric acid | MeVal | N-Methylvaline |
| Des | Desmosine | Nva | Norvaline |

TABLE 1-continued

Modified and/or Unusual Amino Acids

| Abbr. | Amino Acid | Abbr. | Amino Acid |
|---|---|---|---|
| Dpm | 2,2'-Diaminopimelic acid | Nle | Norleucine |
| Dpr | 2,3-Diaminopropionic acid | Orn | Ornithine |
| EtGly | N-Ethylglycine | | |

The presence and the relative proportion N-terminal lactoferrin variants (deletions and/or substitutions) in a preparation of lactoferrin (lactoferrin composition) may be done by determination of the N-terminal amino acid sequence by the process of Edman degradation using standard methods. A relative proportion of N-terminal lactoferrin variant comprise at least 1% of the lactoferrin composition, at least 5% of the lactoferrin composition, at least 10% of the lactoferrin composition, at least 25% of the lactoferrin composition, at least 50% of the lactoferrin composition or any range in between.

In this method, the protein is reacted with phenylisothiocyanate (PITC), which reacts with the amino acid residue at the amino terminus under basic conditions to form a phenylthiocarbamyl derivative (PTC-protein). Trifluoroacetic acid then cleaves off the first amino acid as its anilinothialinone derivative (ATZ-amino acid) and leaves the new amino terminus for the next degradation cycle.

The percentage of N-terminal lactoferrin variant may also be done more precisely by using a Dansylation reaction. Briefly, protein is dansylated using Dansyl chloride reacted with the protein in alkaline conditions (pH 10). Following the Dansylation, the reaction mixtures are dried to pellets, then completely hydrolyzed in 6N HCl. The proportion of N-terminal amino acids are identified by RP HPLC using an in-line fluorometer in comparison with standards made up of known dansylated amino acids.

B. Pharmaceutical Compositions

The present invention is drawn to a composition comprising lactoferrin that is dispersed in a pharmaceutical carrier, which is used to treat cardiovascular disease. The lactoferrin that is contained in the composition of the present invention comprises lactoferrin or an N-terminal lactoferrin variant in which at least the N−1 terminal glycine residue is truncated or substituted. More specifically, the N-terminal lactoferrin variant comprises at least 1% of the composition, at least 5% of the composition, at least 10% of the composition, at least 25% of the composition, at least 50% of the composition or any range in between.

Yet further, the composition comprises lactoferrin in combination with a metal chelator dispersed in a pharmaceutical carrier. Thus, the present invention is drawn to a lactoferrin composition with or without a metal chelator that is dispersed in a pharmaceutical carrier. One of skill in the art understands that both compositions (e.g., lactoferrin alone or lactoferrin in combination with a metal chelator) are within the scope of the present invention and can be used interchangeably depending upon the type of response that is desired. It is envisioned that the addition of a metal chelator to the lactoferrin composition enhances the sequestering of metal ions and thus strengthens the immune system or enhances the effect of lactoferrin.

Metal chelators that can be used in combination with lactoferrin, include the divalent metal chelators, for example, ethylenediaminetetraacetic acid (EDTA), [ethylenebis(oxyethylenenitrilo)]tetraacetic acid (EGTA), 1,2-bis (2-aminophenoxy)ethane-N,N,N',N'-tetraacetic acid (BAPTA), hydroxyethlene triamine diacetic acid, (HEDTA) or any salts thereof. More preferably, EDTA is used in combination with lactoferrin.

Further in accordance with the present invention, the composition of the present invention suitable for administration is provided in a pharmaceutically acceptable carrier with or without an inert diluent. The carrier should be assimilable and includes liquid, semi-solid, e.g., pastes, or solid carriers. Except insofar as any conventional media, agent, diluent or carrier is detrimental to the recipient or to the therapeutic effectiveness of a the composition contained therein, its use in administrable composition for use in practicing the methods of the present invention is appropriate. Examples of carriers or diluents include fats, oils, water, saline solutions, lipids, liposomes, resins, binders, fillers and the like, or combinations thereof.

In accordance with the present invention, the composition is combined with the carrier in any convenient and practical manner, e.g., by solution, suspension, emulsification, admixture, encapsulation, absorption and the like. Such procedures are routine for those skilled in the art.

In a specific embodiment of the present invention, the composition is combined or mixed thoroughly with a semi-solid or solid carrier. The mixing can be carried out in any convenient manner such as grinding. Stabilizing agents can be also added in the mixing process in order to protect the composition from loss of therapeutic activity, e.g., denaturation in the stomach. Examples of stabilizers for use in an the composition include buffers, amino acids such as glycine and lysine, carbohydrates such as dextrose, mannose, galactose, fructose, lactose, sucrose, maltose, sorbitol, mannitol, etc., proteolytic enzyme inhibitors, and the like. Yet further, it is envisioned that divalent metal chelators, for example EDTA, can also be used to stabilize the composition of the present invention. More preferably, for an orally administered composition, the stabilizer can also include antagonists to the secretion of stomach acids.

The composition for oral administration which is combined with a semi-solid or solid carrier can be further formulated into hard or soft shell gelatin capsules, tablets, or pills. More preferably, gelatin capsules, tablets, or pills are enterically coated. Enteric coatings prevent denaturation of the composition in the stomach or upper bowel where the pH is acidic. See, e.g., U.S. Pat. No. 5,629,001. Upon reaching the small intestines, the basic pH therein dissolves the coating and permits the lactoferrin composition to be released and absorbed by specialized cells, e.g., epithelial enterocytes and Peyer's patch M cells.

In another embodiment, a powdered composition is combined with a liquid carrier such as, e.g., water or a saline solution, with or without a stabilizing agent.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Sterile injectable solutions are prepared by incorporating the lactoferrin in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Further, the composition for topical administration which is combined with a semi-solid carrier can be further formulated into a gel ointment. A preferred carrier for the formation of a gel ointment is a gel polymer. Preferred polymers that are used to manufacture a gel composition of the present invention include, but are not limited to carbopol, carboxymethyl-cellulose, and pluronic polymers. Gel polymers prevent denaturation of the composition in the open skin by serum proteases.

The amount of lactoferrin in the present invention may vary from about 1 ng to about 100 g of lactoferrin, more preferably 1 ng to 20 g per day, most preferably 1 µg to 5 g. In preferred embodiments, the composition of the present invention comprises a lactoferrin concentration of about 0.1% to about 100%. The lactoferrin composition may comprise lactoferrin or an N-terminal lactoferrin variant in which at least the N−1 terminal glycine residue is truncated and/or substituted.

More preferably, the composition of the present invention also contains metal chelators, for example, but not limited to ethylenediaminetetraacetic acid (EDTA), [ethylenebis(oxyethylenenitrilo)]tetraacetic acid (EGTA), 1,2-bis(2-aminophenoxy)ethane-N,N,N',N'-tetraacetic acid (BAPTA), hydroxyethlene triamine diacetic acid, (HEDTA) or salts thereof. The amount of the metal chelator in the composition may vary from about 1 ng to about 1 g. A preferred metal chelator is EDTA.

Upon formulation, solutions are administered in a manner compatible with the dosage formulation and in such amount as is therapeutically effective to result in an improvement or remediation of the symptoms. The formulations are easily administered in a variety of dosage forms such as ingestible solutions, drug release capsules and the like. Some variation in dosage can occur depending on the condition of the subject being treated. The person responsible for administration can, in any event, determine the appropriate dose for the individual subject.

C. Treatment or Prophylaxis of Cardiovascular Disease

In accordance with the present invention, the composition provided in any of the above-described pharmaceutical carriers is administered to a subject who has experienced or is at risk of developing cardiovascular disease. Risk factors include, but are not limited to elevated levels of cholesterol or CRP. One of skill in the art can determine the patients who would potentially benefit from a therapeutic agent that would reduce circulating levels of total cholesterol or triglycerides or cardiovascular inflammation. One of skill in the art can determine the therapeutically effective amount of the composition to be administered to a subject based upon several considerations, such as local effects, pharmacodynamics, absorption, metabolism, method of delivery, age, weight, disease severity and response to the therapy.

Oral administration of the composition includes oral, buccal, enteral or intragastric administration. It is also envisioned that the composition may be used as a food additive. For example, the composition is sprinkled on food or added to a liquid prior to ingestion.

In addition to oral administration, the lactoferrin composition can also be administered parenterally, which includes, but is not limited to intradermal, subcutaneous, intramuscular, intraperitoneal, intravenous, intraarterial, intramyocardial, transendocardial, transepicardial, intrathecal, and infusion techniques.

Cardiovascular diseases and/or disorders include, but are not limited to, diseases and/or disorders of the pericardium, heart valves (e.g., incompetent valves, stenosed valves, Rheumatic heart disease, mitral valve prolapse, aortic regurgitation), myocardium (e.g., coronary artery disease, myocardial infarction, heart failure, ischemic heart disease, angina) blood vessels (e.g., hypertension, arteriosclerosis, aneurysm) or veins (e.g., varicose veins, hemorrhoids). In specific embodiments, the cardiovascular disease is atherosclerosis.

In specific embodiments of the present invention, the lactoferrin composition is administered to a subject suffering from or at risk for developing atherosclerosis. Thus, it is envisioned that the lactoferrin composition modulates or reduces the severity and/or incidence of atherosclerosis.

Prophylactic treatment can be administered to those subjects at risk for developing atherosclerosis. One risk factor is an atherogenic lipoprotein profile. For example, a ratio of serum cholesterol to high density lipoproteins of above 5:1 indicates a higher than average risk of developing atherosclerosis. Other factors indicating increased risk for atherosclerosis include a serum cholesterol level of above 240 mg/dl; a high density lipoprotein level below about 35 mg/dl; and a low density lipoprotein level above about 160 mg/dl.

Another embodiment includes treating a human subject with an elevated level of circulating total cholesterol or CRP according to the then medically established guidelines. It is contemplated that the lactoferrin composition of the present invention reduces or attenuates the levels of circulating total cholesterol, low density lipoproteins or very low density lipoproteins. It is contemplated that the lactoferrin composition of the present invention can interfere with how cholesterol enters the circulation either via absorption from food (exogenous pathway) or synthesis by the liver (endogenous pathway).

In further embodiments, the composition is administered in conjunction with an antacid. Thus, an antacid is administered prior or substantially simultaneously with or after oral administration of the composition. The administration of an antacid just prior or immediately following the administration of the composition may help to reduce the degree of inactivation of the lactoferrin in the digestive tract. Examples of appropriate antacids include, but are not limited to, sodium bicarbonate, magnesium oxide, magnesium hydroxide, calcium carbonate, magnesium trisilicate, magnesium carbonate and alumin hydroxide gel.

In a preferred embodiment of the present invention, the composition is administered in an effective amount to decrease, reduce, inhibit or abrogate cardiovascular disease. Thus, a subject is administered a therapeutically effective amount of a lactoferrin composition so that the subject has an improvement in the parameters relating to cardiovascular disease including circulating levels of total cholesterol, HDL, LDL, VLDL, triglycerides and C-reactive protein (CRP). The amount of lactoferrin in the composition may vary from about 1 ng to about 20 g. Preferably, the composition that is orally administered contains the range of 0.5 g to 5 g of lactoferrin per day.

The improvement is any observable or measurable improvement. Thus, one of skill in the art realizes that a treatment may improve the patient condition, but may not be a complete cure of the disease. In certain aspects, the composition is administered in an effective amount to decrease, reduce, inhibit or abrogate excess amounts of cholesterol levels in circulation. A subject requires treatment for cholesterol levels based upon any of the following situations: LDL of 160 mg/ml or greater; LDL of 130–159 mg/ml and also have two or more cardiovascular risk factors; LDL of 100 mg/ml or greater in subjects with coronary heart disease (CHD); triglycerides of 200 mg/dl or higher; total cholesterol of 240 mg/dl or higher or HDL of less than 40 mg/dl. Thus, after administration of lactoferrin, if any of the above conditions improve, then the amount of lactoferrin is considered an effective amount to decrease, reduce, inhibit or abrogate cholesterol levels in the circulation.

Another embodiment is a method of reducing vascular inflammation by administering the lactoferrin composition of the present invention. Vascular inflammation can be tied to a number of the underlying processes contributing to atherosclerosis which include endothelial dysfunction, vascular proliferation and matrix alteration. Recent studies have emphasized the involvement of inflammation in mediating all stages of atherosclerosis. Vascular inflammation is thought to be a consequence of damage to the vascular endothelium and may also involve the proliferation of vascular smooth muscle cells (vsmcs). One precursor of lesion development in humans may be focal accumulation of vsmcs within the intima. In early atherosclerosis, vsmcs may contribute to the development of the atheroma through the production of pro-inflammatory mediators such as monocyte chemoattractant protein 1 and vascular cell adhesion molecule, and through the synthesis of matrix molecules required for the retention of lipoproteins. Inflammation of the vascular endothelium and proliferation of vsmcs may also impact the stability of the plaque through the formation of a firm fibrous cap. Indeed, in lipid-laden lesions in which the fibrous cap is thin and weak, there is evidence of vsmc apoptosis, especially at the "shoulder" region, associated with inflammation. In addition, the local inflammatory milieu can induce expression of collagenase and inhibit expression of proteolytic inhibitors, thus rendering the fibrous cap weak and susceptible to rupture. Lactoferrin, having known anti-inflammatory properties, may thus serve to inhibit the underlying processes associated with the development of atherosclerosis.

In further embodiments, the lactoferrin composition may also reduce vascular spasms or vascular hyper-reactivity. Vascular spasms are a sudden, brief tightening of a blood vessel, which can temporarily reduce blood flow to tissues supplied by that vessel.

Still further, the lactoferrin composition may also promote endothelial integrity or healing. Endothelia are the layer of cells lining the blood vessels. Endothelial dysfunction most commonly refers to impairment of endothelium-dependent vasodilation and widespread abnormalities in endothelial integrity and homeostasis. It is believed that HDLs help maintain endothelial integrity, facilitate vascular relaxation, inhibit blood cell adhesion to vascular endothelium, reduce platelet aggregability and coagulation, and may favor fibrinolysis. The integrity or completeness of the endothelia lining of the vessels is important to preventing/treating the development of plaques and atherosclerosis. Thus, it is envisioned that the lactoferrin composition of the present invention will promote or modulate endothelial integrity or healing.

Yet further, another embodiment is a method of preventing a cardiovascular disease in a subject at risk for developing a cardiovascular disease comprising the step of administering to the subject a lactoferrin composition in an amount sufficient to result in prophylaxis of the cardiovascular disease in the subject. In preferred embodiments, the cardiovascular disease is atherosclerosis. It is envisioned that the lactoferrin composition not only possess therapeutic benefits for those subjects suffering from cardiovascular diseases, but also possess prophylactic properties for those subjects at risk for developing cardiovascular disease. A subject at risk may or may not be cognizant of their disease state or potential disease state and may or may not be aware that they are need of treatment.

Thus, prophylatically, it is envisioned that the lactoferrin composition can reduce any of the following: the levels of circulating total cholesterol, low density lipoproteins (LDL), very low density lipoproteins (VLDL), levels of vascular inflammation, circulating C-reactive protein (CRP), triglycerides, and the proliferation of vascular smooth muscle cells in the subject. Yet further, the lactoferrin composition may also increase the levels of circulating high density lipoproteins (HDL).

Still yet, a further embodiment is a method of enhancing immune response in a subject comprising the step of administering to the subject the composition of the present invention. It is envisioned that the immune response, whether local, systemic or mucosal, is enhanced by lactoferrin stimulating cytokines and/or chemokines. Exemplary cytokines include interleukin-18 and GM-CSF in the gastrointestinal tract, which are known to enhance immune cells or stimulate production of immune cells. For example, interleukin-18 enhances natural killer cells or T lymphocytes. In specific embodiments, interleukin-18 (IL-18) enhances CD4+, CD8+ and CD3+ cells. It is known by those of skill in the art that IL-18 is a $Th_1$ cytokine that acts in synergy with interleukin-12 and interleukin-2 in the stimulation of lymphocyte IFN-gamma production. Other cytokines or chemokines may also be enhanced for example, but not limited to IL-12, IL-1b, MIP-3α, MIP-1α or IFN-γ. Other cytokines or enzymes may be inhibited for example, but not limited to IL-2, IL-4, IL-5, IL-10, TNF-α, or matrix metalloproteinases. It is further contemplated that lactoferrin inhibits the production of TNF-α, which inhibits cells involved in inflammation: It is also envisioned that lactoferrin stimulates interleukin-18 and a $Th_1$ response following oral administration, which inhibits pro-inflammatory cytokines, e.g., IL-4, IL-5, IL-6, IL-8 and TNF-α.

The lactoferrin composition of the present invention can also result in inhibition of a cytokine or chemokine. The cytokines include, but are not limited to interleukin-2 (IL-2), interleukin-4 (IL-4), interleukin-5 (IL-5), interleukin-10 (IL-10), and tumor necrosis factor alpha (TNF-α). Still further, the lactoferrin composition can also inhibit the production of matrix metalloproteinases (MMPs).

In further embodiments, cytokines, for example, interleukin-18 or granulocyte/macrophage colony-stimulating factor, can stimulate the production or activity of immune cells. The immune cells include, but are not limited to T lymphocytes, natural killer cells, NK-T cells, macrophages, dendritic cells, and polymorphonuclear cells. More specifically, the polymorphonuclear cells are neutrophils and the T lymphocytes are selected from the group consisting of CD4+, CD8+ and CD3+ T cells.

In further embodiments, the composition of the present invention also contains metal chelators, for example, but not limited to ethylenediaminetetraacetic acid (EDTA), [ethylenebis(oxyethylenenitrilo)]tetraacetic acid (EGTA), 1,2-bis (2-aminophenoxy)ethane-N,N,N',N'-tetraacetic acid (BAPTA), hydroxyethlene triamine diacetic acid, (HEDTA) or salts thereof.

Treatment regimens may vary as well, and often depend on the health and age of the patient. Obviously, certain types of disease will require more aggressive treatment, while at the same time, certain patients cannot tolerate more taxing regimens. The clinician will be best suited to make such decisions based on the known efficacy and toxicity (if any) of the therapeutic formulations.

In specific embodiments, the composition is given in a single dose or multiple doses. The single dose may be administered daily, or multiple times a day, or multiple times a week, or monthly or multiple times a month. In a further embodiment, the lactoferrin is given in a series of doses. The series of doses may be administered daily, or multiple times a day, weekly, or multiple times a week, or monthly, or multiple times a month.

D. Combination Treatments

In order to increase the effectiveness of the composition, it may be desirable to combine these compositions and methods of the invention with a known agent effective in the treatment or prevention of cardiovascular disease or disorder, for example known agents to treat or prevent atherosclerosis. In some embodiments, it is contemplated that a conventional therapy or agent, including but not limited to, a pharmacological therapeutic agent, a surgical therapeutic agent (e.g., a surgical procedure) or a combination thereof, may be combined with the composition of the present invention.

The composition of the present invention may precede, be co-current with and/or follow the other agent(s) by intervals ranging from minutes to weeks. In embodiments where the composition of the present invention, and other agent(s) are applied separately to a cell, tissue or organism, one would generally ensure that a significant period of time did not expire between the time of each delivery, such that the composition and agent(s) would still be able to exert an advantageously combined effect on the cell, tissue or organism.

Various combination regimens of the composition and one or more agents are employed. One of skill in the art is aware that the composition of the present invention and agents can be administered in any order or combination. In other aspects, one or more agents may be administered substantially simultaneously, or within about minutes to hours to days to weeks and any range derivable therein, prior to and/or after administering the composition.

Administration of the composition to a cell, tissue or organism may follow general protocols for the administration of cardiovascular therapeutics, taking into account the toxicity, if any. It is expected that the treatment cycles would be repeated as necessary. In particular embodiments, it is contemplated that various additional agents may be applied in any combination with the present invention.

A. Pharmacological Therapeutic Agents

Pharmacological therapeutic agents and methods of administration, dosages, etc. are well known to those of skill in the art (see for example, the "Physicians Desk Reference", Goodman & Gilman's "The Pharmacological Basis of Therapeutics", "Remington's Pharmaceutical Sciences", and "The Merck Index, Eleventh Edition", incorporated herein by reference in relevant parts), and may be combined with the invention in light of the disclosures herein. Some variation in dosage will necessarily occur depending on the condition of the subject being treated. The person responsible for administration will, in any event, determine the appropriate dose for the individual subject, and such individual determinations are within the skill of those of ordinary skill in the art.

Non-limiting examples of a pharmacological therapeutic agent that may be used in the present invention include an antihyperlipoproteinemic agent, an antiarteriosclerotic agent, an anti-cholesterol agent, an anti-inflammatory agent, an antithrombotic/fibrinolytic agent, a blood coagulant, an antiarrhythmic agent, an antihypertensive agent, or a vasopressor. In certain aspects of the present invention, anti-cholesterolemic agents are used in combination with the composition of the present invention. Anti-cholesterol agents include but are not limited to HMG-CoA Reductase inhibitors, cholesterol absorption inhibitors, bile acid sequestrants, nicotinic acid and derivatives thereof, fibric acid and derivatives thereof. HMG-CoA Reductase inhibitors include statins, for example, but not limited to atorvastatin calcium (Lipitor), cerivastatin sodium (Baycol®), fluvastatin sodium (Lescol®), lovastatin (Advicor®), pravastatin sodium (Pravachol®), and simvastatin (Zocor®). Agents known to reduce the absorption of ingested cholesterol include, for example, exetimibe (Zetia®). Bile acid sequestrants include, but are not limited to cholestyramine, cholestipol and colesevalam. Other anti-cholesterol agents include fibric acids and derivatives thereof (e.g., gemfibrozil, fenofibrate and clofibrate); nicotinic acids and derivatives thereof (e.g., nician, lovastatin) and agents that extend the release of nicotinic acid, for example niaspan. Anti-inflammatory agents include, but are not limited to non-steroidal anti-inflammatory agents (e.g., naproxen, ibuprofen, celeoxib) and sterodial anti-inflammatory agents (e.g., glucocorticoids).

B. Surgical Therapeutic Agents

In certain aspects, a therapeutic agent may comprise a surgery of some type, which includes, for example, preventative, diagnostic or staging, curative and palliative surgery. Surgery, and in particular a curative surgery, may be used in conjunction with other therapies, such as the present invention and one or more other agents.

Such surgical therapeutic agents for cardiovascular diseases and disorders are well known to those of skill in the art, and may comprise, but are not limited to, performing surgery on an organism, providing a cardiovascular mechanical prostheses, angioplasty, coronary artery reperfusion, catheter ablation, providing an implantable cardioverter defibrillator to the subject, mechanical circulatory support or a combination thereof. Non-limiting examples of a mechanical circulatory support that may be used in the present invention comprise an intra-aortic balloon counterpulsation, left ventricular assist device or combination thereof.

E. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Cholesterol Reduction by Recombinant Human Lactoferrin (rhLF)

Healthy adult human volunteers were administered a liquid formulation of either rhLF or placebo for seven days. Fasting serum was collected at baseline (prior to administration of rhLF) and at the end of study (Day 10) and levels of total cholesterol determined. All subjects were housed in an in-patient setting for the duration of the study and received similar diets.

In this clinical trial, human subjects treated with placebo drug experienced a rise in serum cholesterol. RhLF treated subjects in a similar setting and receiving a similar diet, experienced a reduction in total cholesterol. FIG. 1 shows that administration of rhLF for just seven days resulted in 14% reduction in total cholesterol (P<0.05).

Example 2

Reduction of C-Reactive Protein (CRP) by Recombinant Human Lactoferrin (rhLF)

Healthy adult human volunteers were administered a liquid formulation of rhLF or placebo for seven days. RhLF was administered for a total of seven days. Serum was collected on Day 1 and Day 7 of rhLF administration and assayed for CRP using a high sensitive assay.

Figure 2:
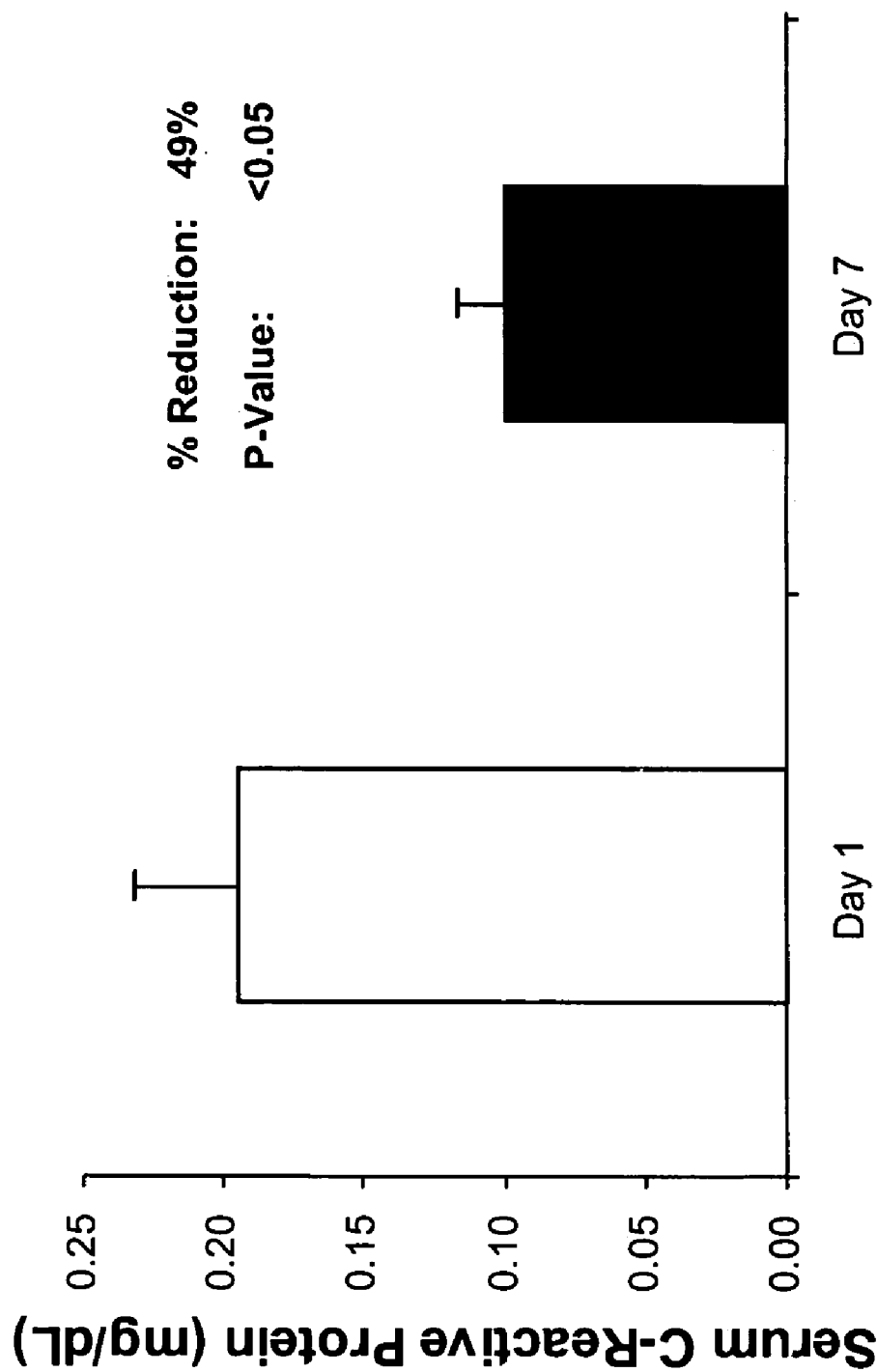
FIG. 2 shows the reduction of C-reactive protein in subjects receiving oral rhLF for seven days.

A total of six subjects had Day 1 CRP levels that were measurable by the high sensitive assay (>0.07 mg/dL). Five out of the six subjects showed a reduction in CRP with the sixth patient showing no change. As shown in FIG. 2, the six evaluable subjects showed an average of 49% reduction in CRP levels (P<0.05) as well as a 17% reduction in their cardiovascular risk.

Example 3

RhLF Effect on Hyperlipidemia in Mice

Figures 3A, 3B:
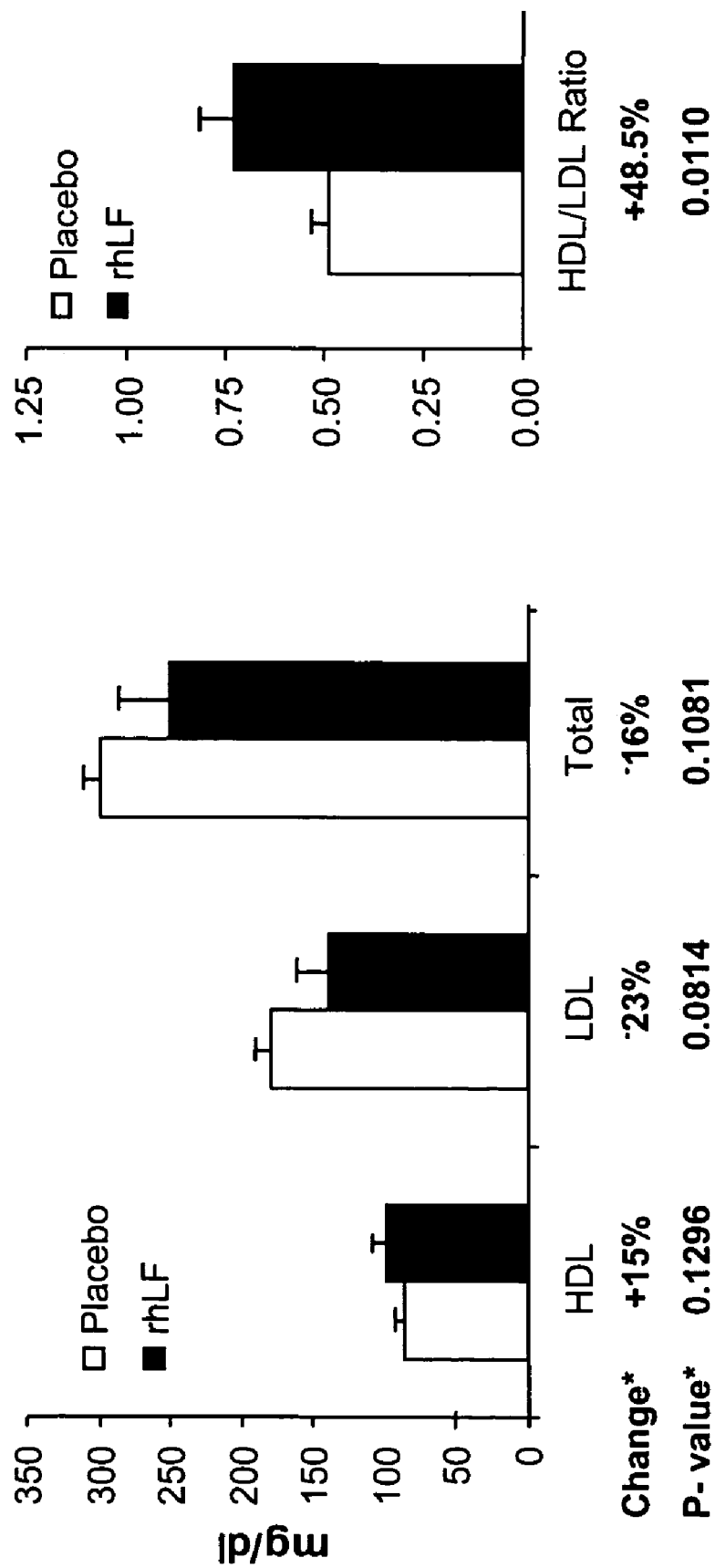
FIG. 3A and FIG. 3B show the effect of rhLF on hyperlipidemia in mice.

The effect of oral rhLF was tested in a mouse model of hyperlipidemia induced by the mice being fed a high cholesterol-fat diet for 14 days (2 g lard, 8 g coconut oil, 1 g cholesterol, 0.3 g cholic acid per 100 g of feed and 88.7 g standard chow). The hyperlipidemic mice were administered either placebo vehicle or rhLF (1000 mg/kg) twice a day for seven days. Twenty-four hours after the last dose, serum was obtained from individual fasting animals and assayed for total cholesterol, HDL and LDL. The rhLF treated mice showed a trend toward decrease in total cholesterol (16%) and LDL cholesterol (23%) and an increase in HDL cholesterol (15%). The HDL/LDL ratio was increased by 48.5% and was statistically significant (FIG. 3).

Example 4

Dose Effects of RhLF on Hyperlipidemia in Mice

Mice were rendered hypercholesteremic by administration of a high cholesterol diet for fourteen days. Animals received rhLF (32.5, 150 or 500 mg/kg) or placebo administered orally twice a day for 14 consecutive days. Twenty-four hours after the last dose of drug, fasting animals were sacrificed and serum total cholesterol (Total, high density lipoprotein (HDL), low density lipoprotein (LDL) and Total/HDL) ratio were determined.

High cholesterol diet used to induce hyperlipidemia consisted of 2 g lard, 8 g coconut oil, 1 g cholesterol, 0.3 g cholic acid per 100 g of feed and 88.7 g standard chow.

At the doses tested, a beneficial effect from rhLF was observed after 14 days treatment. No dose dependence was observed. As shown in FIG. 4, all doses of rhLF decreased both total cholesterol and LDL-cholesterol relataive to placebo treated animals. A statistically significant decrease in LDL-cholesterol was observed (25% decrease, $p<0.05$) when all the rhLF treated animals were compared to the placebo treated animals. There was also a decrease in total cholesterol (19% reduction; $p=0.0594$).

Example 5

Effect of Oral rhLF with Lovastatin on Hyperlipidemia in Mice

Figure 5:
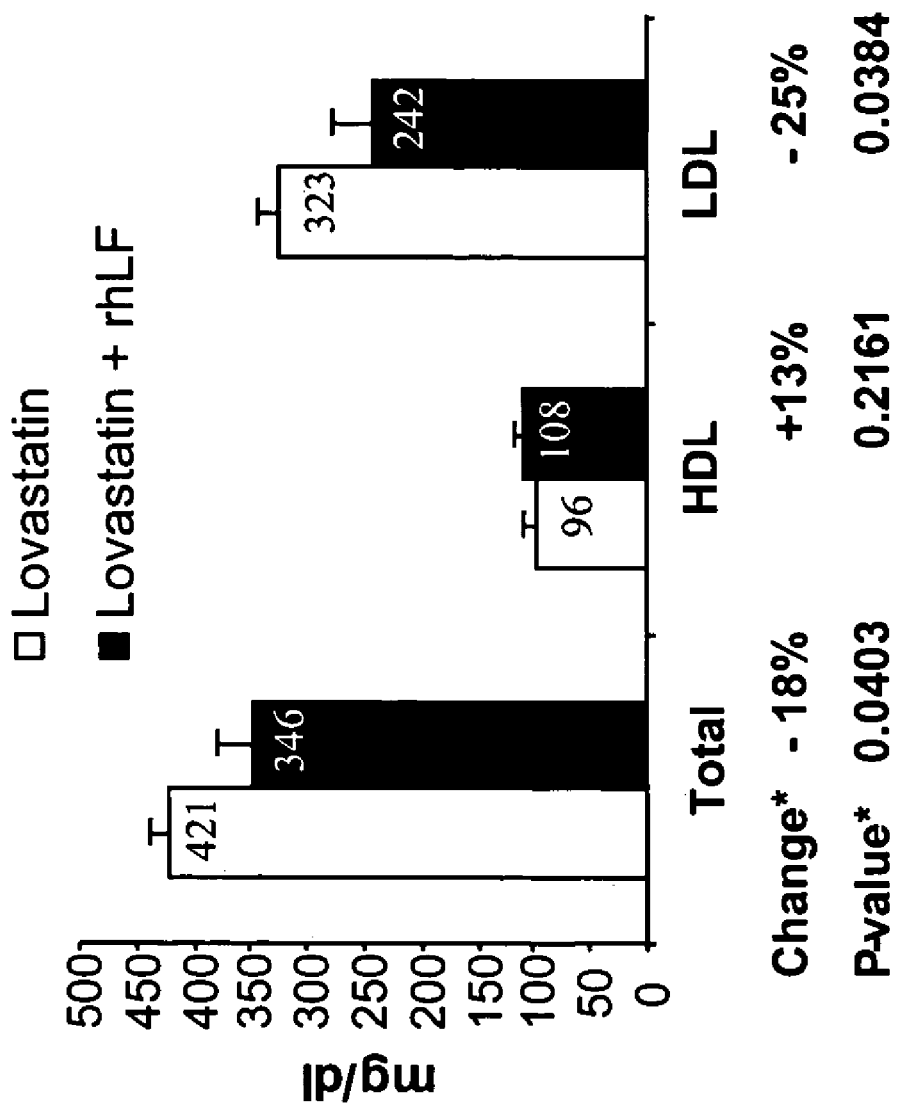
FIG. 5 shows the effect of oral rhLF with lovastatin on hyperlipidemia in mice.

The ability of oral rhLF to potentiate the effect of lovastatin in the induced hyperlipidemia model was also tested. Hyperlipidemic mice were treated with lovastatin (15 mg/kg) alone or in combination with rhLF (500 mg/kg b.i.d.) for seven days. Mice treated with lovastatin plus lactoferrin had astatistically significant ($p<0.05$) reduction in both Total Cholesterol and LDL-Cholesterol relative to the lovastatin treated mice (18% and 25% respectively) and a 13% increase in HDL cholesterol (FIG. 5).

Example 6

Reduction of Systemic Inflammation in Murine Models

Mice and rats with elevated systemic or cardiovascular inflammation are administered placebo or rhLF for 7, 14 or 28 days and markers of inflammation including CRP are assayed.

Example 7

Reduction of Cholesterol with rhLF Therapy

Human patients with elevated levels of cholesterol (>200 mg/dL) are administered: rhLF or placebo for 14, 28 and 90 days. Fasting serum is assayed for total cholesterol, HDL, LDL, VLDL, and triglycerides.

Example 8

Reduction of CRP with rhLF Therapy

Human patients with elevated levels of CRP are administered rhLF or placebo for 14, 28 and 90 days. Serum is assayed for CRP and other markers of inflammation.

Example 9

Dose Ranging Study of rhLF in the Reduction of Cholesterol and CRP

Human patients with elevated levels of cholesterol (>200 mg/dL) are given placebo or ascending doses of rhLF for 30, 90 and 180 days. Fasting serum is assayed for total cholesterol, HDL, LDL, VLDL, triglycerides and CRP.

Example 10

Reduction of Cholesterol and CRP with rhLF in Combination Therapy

Human patients with elevated levels of cholesterol (>200 mg/dL) are administered an approved cholesterol reducing drug either alone or in combination with rhLF for 30, 90 and 180 days. Cholesterol reducing drugs tested include Lipitor® (atorvastatin), Zocor® (simvastatin), and Zetia® (ezetimibe). Fasting serum is assayed for total cholesterol, HDL, LDL, VLDL, triglycerides and CRP.

Example 11

Reduction of Cardiovascular Incidence with rhLF Alone or in Combination Therapy

Human patients considered at an elevated risk for cardiovascular accidents (including stroke and heart attacks) are treated with rhLF alone, approved drugs alone or a combination of rhLF and an approved drug. Fasting serum is assayed for total cholesterol, HDL, LDL, VLDL, triglycerides and CRP. Incidence and severity of stroke and heart attacks and incidence of mortality are also measured.

REFERENCES CITED

All patents and publications mentioned in the specifications are indicative of the levels of those skilled in the art to which the invention pertains. All patents and publications are herein incorporated by reference to the same extent as if each individual publication was specifically and individually indicated to be incorporated by reference.

U.S. Pat. No. 5,571,691
U.S. Pat. No. 5,571,697
U.S. Pat. No. 5,571,896
U.S. Pat. No. 5,629,001
U.S. Pat. No. 6,080,559
U.S. Pat. No. 5,919,913
U.S. Pat. No. 6,228,614
U.S. Pat. No. 6,455,687
U.S. Pat. No. 6,277,817
U.S. Pat. No. 6,066,469
U.S. Pat. No. 6,100,054
U.S. Pat. No. 6,333,311

Although the present invention and its advantages have been described in detail, it should be understood that various changes, substitutions and alterations can be made herein without departing from the invention as defined by the appended claims. Moreover, the scope of the present application is not intended to be limited to the particular embodiments of the process, machine, manufacture, composition of matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

What is claimed is:

1. A method of treating atherosclerosis or vascular inflammation comprising: orally administering to a subject an effective amount of lactoferrin; and administering an antacid in conjunction with said lactoferrin.

2. The method of claim 1, wherein said lactoferrin reduces levels of circulating total cholesterol, low density lipoproteins (LDL), very low density lipoproteins (VLDL), or triglycerides in said subject.

3. The method of claim 1, wherein said lactoferrin increases the levels of circulating high density lipoproteins (HDL) in said subject.

4. The method of claim 1, wherein said lactoferrin reduces the levels of vascular inflammation in said subject.

5. The method of claim 1, wherein said lactoferrin reduces circulating C-reactive protein (CRP) in said subject.

6. The method of claim 1, wherein said lactoferrin reduces the proliferation of vascular smooth muscle cells in said subject.

7. The method of claim 1, wherein said lactoferrin reduces vascular spasm or vascular hyper-reactivity in said subject.

8. The method of claim 1, wherein said lactoferrin promotes endothelial integrity or healing in said subject.

9. The method of claim 1, wherein said lactoferrin is dispersed in a pharmaceutically acceptable carrier.

10. The method of claim 1, wherein said lactoferrin is mammalian lactoferrin.

11. The method of claim 10, wherein said lactoferrin is human or bovine.

12. The method of claim 1, wherein said lactoferrin is recombinant lactoferrin.

13. The method of claim 1 further comprising administering the lactoferrin in a delayed release formulation.

14. The method of claim 13 where the lactoferrin release occurs in the small intestine.

15. The method of claim 13 where the lactoferrin release occurs in the large intestine.

16. The method of claim 1, wherein the amount of the lactoferrin that is administered is about 1 ng to about 20 g per day.

17. The method of claim 1, wherein the amount of the lactoferrin that is administered is about 0.1 g to about 5 g per day.

18. The method of claim 1, wherein said lactoferrin reduces the production or activity of pro-inflammatory cytokines.

19. The method of claim 1, further comprising administering a lactoferrin in combination with an anti-cholesterol agent or an anti-inflammatory agent.

20. The method of claim 19, wherein the anti-cholesterol agent is selected from the group consisting of cholesterol absorption inhibitors, bile acid sequestrants, nicotinic acid, fibric acids and HMG-coA reductase inhibitors.

21. The method of claim 20, wherein the bile acid sequestrants are selected from the group consisting of cholestryramine, cholestipol and colesevalam.

22. The method of claim 20, wherein the fibric acids are selected from the group consisting of gemfibrozil, fenofibrate and clofibrate.

23. The method of claim 20, wherein the HMG-coA reductase inhibitors are selected from the group consisting of lovastatin, pravastatin, simvastatin, fluvastatin, atorvastatin and cerivastatin.

* * * * *